United States Patent
Brooks et al.

(10) Patent No.: US 6,750,661 B2
(45) Date of Patent: Jun. 15, 2004

(54) METHOD AND APPARATUS FOR CONTROLLABLY EFFECTING SAMPLES USING TWO SIGNALS

(75) Inventors: Carlton F. Brooks, Menlo Park, CA (US); Morten Juel Jensen, San Francisco, CA (US); Seth Stern, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 0 days.

(21) Appl. No.: 10/293,238

(22) Filed: Nov. 12, 2002

(65) Prior Publication Data

US 2003/0094953 A1 May 22, 2003

Related U.S. Application Data

(60) Provisional application No. 60/332,990, filed on Nov. 13, 2001.

(51) Int. Cl.⁷ .................. G01R 27/08; G01N 27/02; G01K 7/00
(52) U.S. Cl. .................. 324/693; 324/692; 324/441; 374/163; 204/602
(58) Field of Search ................ 324/441, 71.1, 324/525, 609, 692, 693, 444; 204/473, 474, 477, 408, 602, 607; 435/285.2; 374/114, 163; 422/82.01, 82.02

(56) References Cited

U.S. PATENT DOCUMENTS

| | | | |
|---|---|---|---|
| 4,947,468 A | * 8/1990 | Nelson | 324/453 |
| 5,455,513 A | * 10/1995 | Brown et al. | 324/445 |
| 5,589,047 A | 12/1996 | Coster et al. | 204/450 |
| 5,644,239 A | * 7/1997 | Huang et al. | 324/439 |
| 5,779,868 A | 7/1998 | Parce et al. | 204/604 |
| 5,800,690 A | 9/1998 | Chow et al. | 204/451 |
| 5,942,443 A | 8/1999 | Parce et al. | |
| 5,965,001 A | 10/1999 | Chow et al. | 435/91.2 |
| 5,965,410 A | * 10/1999 | Chow et al. | 435/91.2 |
| 6,132,580 A | 10/2000 | Mathies et al. | 204/453 |
| 6,143,152 A | 11/2000 | Simpson et al. | 204/451 |
| 6,150,107 A | 11/2000 | Glazer et al. | 435/6 |
| 6,171,850 B1 | 1/2001 | Nagle et al. | |
| 6,261,431 B1 | 7/2001 | Mathies et al. | 204/601 |
| 6,284,525 B1 | 9/2001 | Mathies et al. | 435/287.2 |
| 6,306,590 B1 | 10/2001 | Mehta et al. | 435/6 |
| 6,437,551 B1 | 8/2002 | Krulevitch et al. | |
| 6,448,794 B1 | 9/2002 | Cheng et al. | |

FOREIGN PATENT DOCUMENTS

WO    WO 96/04547    2/1996

OTHER PUBLICATIONS

Manz, et al. Trends in Anal. Chem. (1990) 10(5):144–149.

Manz, et al. Adv. In Chromatog. (1993) 33:1–66.

* cited by examiner

*Primary Examiner*—Anjan K. Deb
(74) *Attorney, Agent, or Firm*—Donald R. McKenna; Quine Intellectual Property Law Group

(57) ABSTRACT

Methods and systems for effecting a parameter and detecting a parameter using two electric signal in a conductive path are described.

66 Claims, 11 Drawing Sheets

METHOD AND APPARATUS FOR CONTROLLABLY EFFECTING SAMPLES USING TWO SIGNALS

This application claims priority from provisional patent application No. 60/332,990 filed Nov. 13, 2001, which is incorporated herein by reference.

All documents referenced herein are incorporated in their entirety by reference for all purposes.

This application may be related to other patent applications and issued patents assigned to the assignee indicated above. These applications and issued patents are incorporated herein by reference to the extent allowed under applicable law.

FIELD OF THE INVENTION

The present invention generally relates to methods and/or systems for precisely controlling and measuring heating. More particularly, the present invention provides a technique, including methods and devices, for providing and controlling heat to samples in a channel of a micro scale sample handling system. Merely by way of example, the invention is applied to a polymerase chain reaction process, commonly termed PCR, performed in a microfluidic system or device but it will be recognized that the invention has a much wider range of applicability. The invention according to further embodiments also provides techniques for monitoring and controlling a variety of process parameters using impedance and/or conductance measurements.

According to further embodiments, the invention relates to a computer method and/or system for precisely determining temperature and/or controlling heating in specific devices.

BACKGROUND OF THE INVENTION

The discussion of any work, publications, sales, or activity anywhere in this submission, including in any documents submitted with this application, shall not be taken as an admission by the inventors that any such work constitutes prior art. The discussion of any activity, work, or publication herein is not an admission that such activity, work, or publication existed or was known in any particular jurisdiction.

There has been a growing interest in the manufacture and use of microscale systems for the acquisition of chemical and biochemical information. Techniques commonly associated with the semiconductor electronics industry, such as photolithography, wet chemical etching, etc., are being used in the fabrication of microscale systems, such as microfluidic systems. The term "microfluidic" refers generally to a system or device or "chip" having channels and chambers which are generally fabricated at the micron or submicron scale, e.g., having at least one cross-sectional dimension in the range of from about 0.1 $\mu$m to about 500 $\mu$m. Early discussions of the use of planar chip technology for the fabrication of microfluidic systems are provided in Manz et al., Trends in Anal. Chem. (1990) 10(5):144–149 and Manz et al., Adv. in Chromatog. (1993) 33:1–66, which describe the fabrication of such fluidic devices and particularly microcapillary devices, in silicon and glass substrates.

Applications of microscale and/or microfluidic systems are myriad. For example, International Patent Appln. WO 96/04547, published Feb. 15, 1996, describes the use of microfluidic systems for capillary electrophoresis, liquid chromatography, flow injection analysis, and chemical reaction and synthesis. U.S. application Ser. No. 08/671,987, entitled "HIGH THROUGHPUT SCREENING ASSAY SYSTEMS IN MICROSCALE FLUIDIC DEVICES", filed on Jun. 28, 1996 by J. Wallace Parce et al., and assigned to the present assignee, discloses wide ranging applications microfluidic systems in rapidly assaying large number of compounds for their effects on chemical, and preferably, biochemical systems. The phrase, "biochemical system", generally refers to a chemical interaction which involves molecules of the type generally found within living organisms. Such interactions include the full range of catabolic and anabolic reactions which occur in living systems including enzymatic, binding, signaling and other reactions. Biochemical systems of particular interest include, e.g., receptor-ligand interactions, enzyme-substrate interactions, cellular signaling pathways, genetic analysis, transport reactions involving model barrier systems (e.g., cells or membrane fractions) for bio-availability screening, and a variety of other general systems.

Many chemical or biological systems also benefit from control over processing parameters such as temperature, concentration of reagents, buffers, salts and other materials, and the like. In particular, some chemical or biological systems require processes to be carried out at controlled and/or controllably varied temperature. In providing such a controlled temperature in miniaturized fluidic systems, external heating elements have generally been used. Such heating elements typically include external resistive heating coils or material, which provide heat to the fluidic system in a conductive manner. This heating unit attaches itself directly to an external portion of the chip to globally heat the chip and to provide a uniform temperature distribution to be present on the chip. This external heating unit, however, is cumbersome. It also complicates chip manufacturing and often affects quality and reliability of the chip. Additionally, the external heating element can fail and generally cannot effectively control heat supplied to the chip, which can cause undesirable temperature gradients and fluctuations in the chip. Accordingly, the external heating element applied to a chip is limited and can be unreliable in controlling process temperature in the chip.

Larger scale temperature controllers have also been used to control reaction temperatures within a reaction vessel, including, e.g., hot-plates, water baths, and the like. Such controllers are not well suited to providing accurate control of temperature within a microfluidic system. In fact, such global heating systems heat the entire material region of the microfluidic device and cannot be used to selectively apply heat to specific regions of the microfluidic device, e.g., specific channels or chambers. Additionally, these large temperature controllers, e.g., hot plates, often require large heating elements, which transfer heat via conduction. These heating elements possess a large characteristic response time, which often relates to a long time to heat or cool material within a reaction vessel in contact therewith in some applications.

SUMMARY OF THE INVENTION

Various strategies have been proposed for providing heating in a microscale (such as microfluidic) device. Among these strategies, three of particular interest to the present invention are (1) Joule (or electrolytic) heating, (2) in-channel resistive heating, and (3) proximal resistive heating. In each of these types of heating, an electric signal is used to provide energy. In Joule heating, the electric signal is passed directly through the sample to be heated (which generally must be an electrolytic material, thus the alternative name electrolytic heating.) Electrical energy is converted to heat as it passes through the sample. In resistive heating, a separate conductor (such as a metal or semiconductor channel) is used to carry the electric signal. The impedance and/or resistance of this separate conductor causes the conductor to heat due to electric signal flow. This heat is then transferred by heat conduction to a sample in a microscale device channel or region. In in-channel resistive heating, one or more heating elements is placed in the channel, possibly in contact with the sample material. In proximal resistive heating, one or more heating elements is placed near the channel.

Various of the above general types of heating strategies has been proposed using either DC electrical signals or AC electrical signals. It has also been proposed to detect effects of heating (such as the temperature) or other effects using conductance or impedance of the applied electrical signal. However, there is a continuing need for refined and improved techniques for effecting and/or detecting heating or other parameters in microscale devices. A number of earlier patents discuss various aspects related to the operation and/or construction of microfluidic systems. An example of these include U.S. Pat. No. 5,965,410 (Electrical current for controlling fluid parameters in microchannels); U.S. Pat. No. 5,779,868; U.S. Pat. No. 5,800,690; U.S. Pat. No. 6,306,590; and U.S. Pat. No. 6,171,850 (Integrated devices and systems for performing temperature controlled reactions and analyses).

According to the present invention, two different signals are used one signal to provide energy for heating (or, in alternative embodiments, effecting other parameters) and another signal at a different frequency used as a probe to measure the effect on the parameter. The second signal, in specific embodiments, is an electrical signal having a different frequency than the signal used for heating. Thus, in specific embodiments, the invention provides a mechanism that allows a detection or probe signal to remain separated from an effector signal without requiring physically separate conductive paths.

Specific embodiments according to the invention include (1) a joule heating system and/or method wherein the effector signal and probe signal are signals through an electrolytic sample medium (2) an in-channel resistive heating system and/or method wherein the effector signal and probe signal are signals through an in-channel electrical conductor; and (3) a proximal resistive heating system and/or method wherein the effector signal and probe signal are signals through an electrical conductor proximal to a channel. Specific embodiments according to the invention also include (1) a heating system and/or method wherein the effector signal is a DC signal and the probe signal is a distinguishable AC, e.g. of about 10 Hz; and (2) a heating system and/or method wherein the effector signal is a higher frequency AC signal and the probe signal is a distinguishable lower frequency AC signal.

While various combinations of the above characteristics are possible, according to specific embodiments of the invention a DC heating signal is generally not used when the signal passes through the sample (joule heating).

In various embodiments, the present invention can be embodied in a microfluidic system. In particular, such a system comprises a substrate having at least a first fluid-filled (as used herein, fluid also includes a gel) microscale channel disposed therein. The system also includes a means for generating or receiving the first and second signals for controlling temperature of the fluid in the first portion of the channel.

In a related aspect, the present invention provides a microfluidic system having one or more thermal elements included therein. The system comprises a first channel defined in a substrate, where the channel includes a first end and a second end. A first energy source is provided coupled between the first end and the second end of the channel. The first energy source is applied such that a portion of said material is heated in a portion of said first capillary channel.

A second energy source is also provided coupled to the fluid in the first channel, whereby a signal from the second energy source can be monitored to measure a characteristic of the channel and/or material therein. In further embodiments, this measurement can be used to control adjustment of parameters in the fluid. Typically, a third energy source can also be provided coupled to the channel, whereby a signal from the third energy source is further set at a current or voltage such that a fluid is pumped through said first channel.

In still another related aspect, the present invention provides a microfluidic system, that comprises a capillary channel comprising a first end and a second end, and at least two signal (e.g., energy) sources (or a single source divided or filtered to provide at least two different signals) coupled between the first end and the second end. The source(s) provide voltage and/or current signals coupled to the channel and/or material such that a portion of a fluid is heated in a portion of the capillary channel using one signal and such that parameters, such as temperature, are measured by a second signal.

In a further related aspect, the present invention provides a microfluidic system, which comprises a capillary channel defined in a substrate, the channel comprising fluid therein, wherein the capillary channel has a region whereupon fluid in the region is selectively heated using a voltage bias applied to the fluid in the capillary channel, with temperature measured using a second signal applied to the fluid in the capillary channel.

In a further related aspect, the present invention also provides a multi-port, microfluidic device, which comprises a substrate having a first fluid-filled channel region defined therein. The substrate includes at least a first port and a second port for transporting a material therebetween, and a second channel region defined in the substrate for applying electric current for heating fluid between the first and second ports and for applying a signal for measuring temperature in the fluid.

The present invention also provides a computer program product for operating a microfluidic system in accordance with other aspects of the present invention. In particular, the computer program comprises a computer readable memory including a code that directs an energy source to adjust an electric current or voltage to a channel comprising a fluid therein, to heat the fluid to a selected elevated level and for measuring temperature using a second applied electrical signal.

The present invention also provides methods of controlling temperatures in microfluidic systems as herein described.

Aspects of one illustrative embodiment of a the invention is described below as it might be implemented on a general purpose computer using a suitable programming language such as Java, C++, Cobol, C, Pascal, Fortran., PL 1, LISP, assembly, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system- and business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Other Features & Benefits

The invention and various specific aspects and embodiments will be better understood with reference to the following drawings and detailed descriptions. In different figures, similarly numbered items are intended to represent similar functions within the scope of the teachings provided herein. In some of the drawings and detailed descriptions below, the present invention is described in terms of the important independent embodiment of a microfluidic device or system. This should not be taken to limit the invention, which, using the teachings provided herein, can be applied to other situations in which it is desired to control the heating of fluids. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic and/or electronic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Java, Java-script, HTML, XML, dHTML, assembly or machine code programming, etc. All references, publications, patents, and patent applications cited herein are hereby incorporated by reference in their entirety for all purposes.

DETAILED DESCRIPTION OF THE INVENTION

1. Glossary

Figure 1:
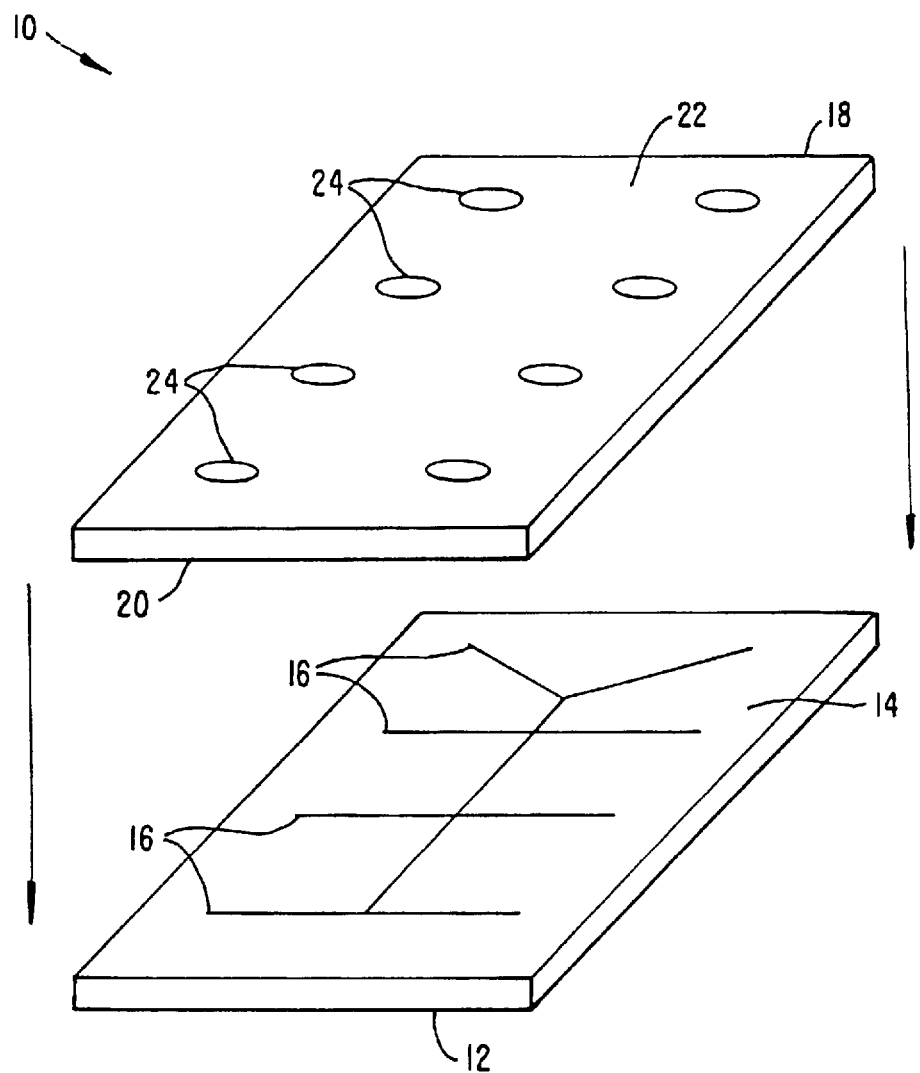
FIG. 1 is a simplified schematic illustration of an embodiment of a microfluidic system according to specific embodiments of the present invention.

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

Unless defined otherwise, technical and scientific terms used herein have meanings as commonly understood by one of ordinary skill in the art to which the invention pertains. Although any methods and materials similar or equivalent to those described herein can be used in practice or for testing of the present invention, the preferred materials and methods are described herein.

In describing and claiming the present invention, the following terminology will be used in accordance with the definitions set out below.

The term "microfluidic device" as used herein refers to a device for performing nanoliter-scale reactions, typically containing one or more microscale channels. The term "microscale channel", or "microchannel," refers to one or more fluid passages, chambers, conduits, cavities, channels, channel networks, or reservoirs which have at least one internal cross-sectional dimension, e.g., depth, width, length, diameter, generally for example in the range of about 0.1 micro meters to about 500 micro meters.

As used herein, the terms "microscale" or "microfabricated" generally refers to structural elements or features of a device which have at least one fabricated dimension in the range of from about 0.1 micro meters to about 500 micro meters. Thus, a device referred to as being microfabricated or microscale will include at least one structural element or feature having such a dimension. When used to describe a fluidic element, such as a passage, chamber or conduit, the terms "microscale", "microfabricated" or "microfluidic" generally refer to one or more fluid passages, chambers or conduits which have at least one internal cross-sectional dimension, e.g., depth, width, length, diameter, etc., that is less than 500 µm, and typically between about 0.1 µm and about 500 µm. In the devices of the present invention, the microscale channels or chambers preferably have at least one cross-sectional dimension between about 0.1 µm and 200 µm, more preferably between about 0.1 µm and 100 µm, and often between about 0.1 µm and 20 µm.

2. Microfluidic Systems

Microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication. Body structures may be integrated structures, or may be aggregations of multiple separate parts that fit together to form the aggregate body structure.

Typically, the body structure of the microfluidic devices described herein comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates a two-layer body structure 10, for a microfluidic device. In preferred aspects, the bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents. Although preferred substrates are planar in structure, it will be appreciated that a variety of substrate conformations may be utilized, including concave or convex structures, tubular structures, e.g., capillaries, and the like.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, U.S. Pat. No. 5,885,470, and which is incorporated herein by reference in its entirety for all purposes. Further, such alternate substrates may be in any of a variety of conformations, e.g., planar, tubular, concave, convex, or the like.

The channels and/or chambers of the microfluidic devices are typically fabricated into the upper surface of the bottom substrate or portion 12, as microscale grooves or indentations 16, using the above described microfabrication techniques. In specific embodiments according to the present invention using resistive heating, grooves or indentations 16 can be associated with in-channel or proximal heating elements using microfabrication techniques.

The top portion or substrate 18 also comprises a first planar surface 20, and a second surface 22 opposite the first planar surface 20. In the microfluidic devices prepared in accordance with methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

It will be further understood that microfabrication techniques can include fabrication of electrical conducting paths either in the channels or proximal to the channels. These electrical conducting paths can comprise metals and/or other conducting and/or semiconducting materials.

In some embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. patent application Ser. Nos. 08/761,575 and 08/760,446 each of which was filed on Dec. 6, 1996, and is hereby incorporated by reference in its entirety for all purposes.

In further embodiments, the devices, methods and systems described herein, can employ electrokinetic material transport systems, and preferably, controlled electrokinetic material transport systems. As used herein, "electrokinetic material transport systems" include systems which transport and direct materials within an interconnected channel and/or chamber containing structure, through the application of electrical fields to the materials, thereby causing material movement through and among the channel and/or chambers.

Although the preferred aspects of the present invention generally employ electrokinetic transport of materials in microfluidic systems, it is easily recognized that the heating and control aspects of the present invention are readily adaptable to systems utilizing other material transport systems. For example, pressure based or pneumatic flow systems using pumps and/or pressure sources external to the microfluidic device can be used in conjunction with the heating, sensing and control aspects of the present invention. Similarly, integrated microfluidic devices, e.g., incorporating microfabricated pump and valve structures, integrated into the device, are also readily adaptable for use with these heating and control systems.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure, which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel will cause the proton sheath to move in the direction of the voltage drop, i.e., toward the negative electrode, pulling the bulk fluid along with it.

"Controlled electrokinetic material transport and direction", as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

Figure 2:
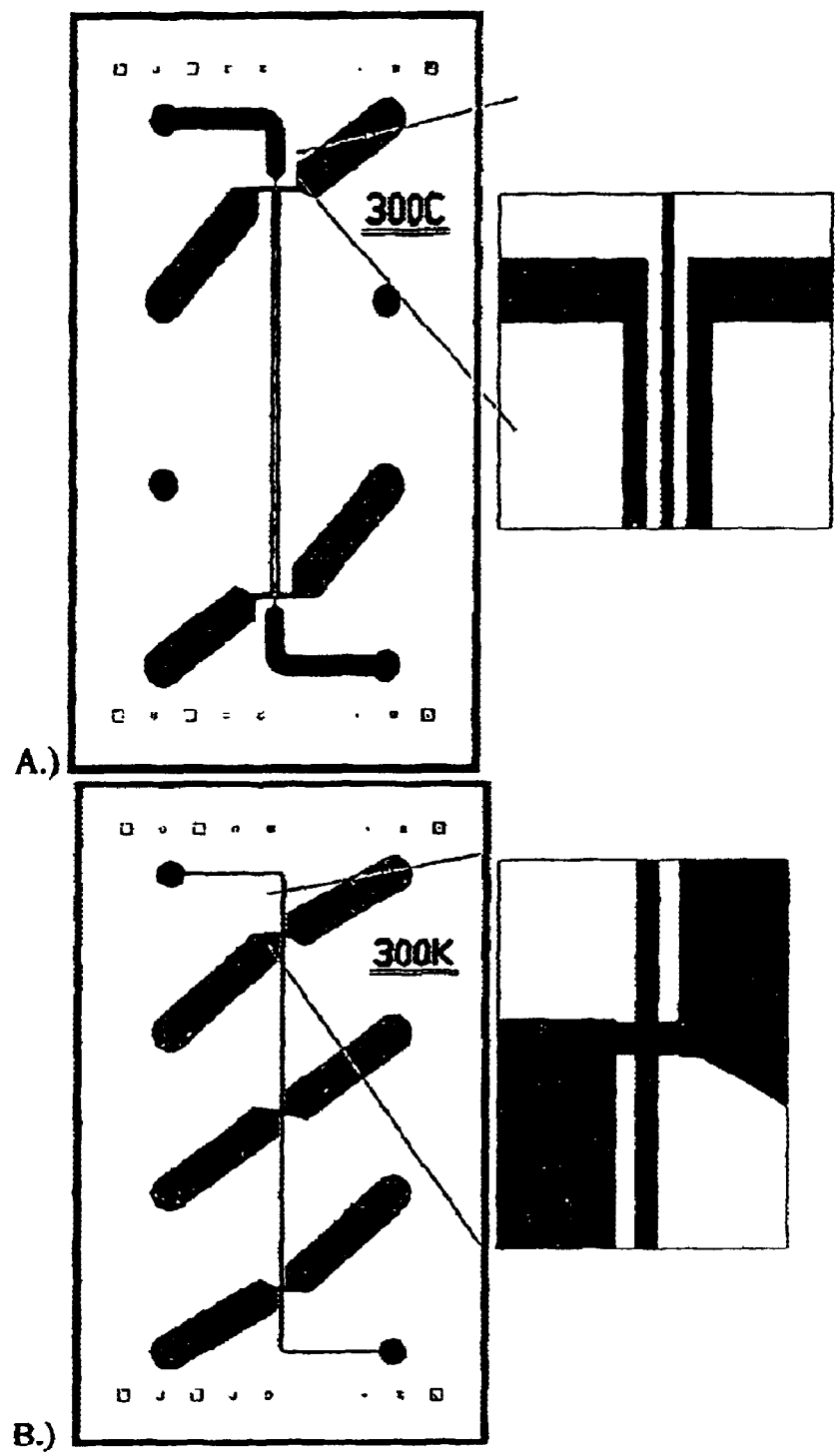
FIG. 2 is a simplified schematic illustration of two designs embodiment of a microfluidic device with resistive heating according to specific embodiments of the present invention.

FIG. 2 is a simplified schematic illustration of two designs embodiment of a microfluidic device with resistive heating according to specific embodiments of the present invention. These designs are provided as examples, and many other configurations are possible according to specific embodiments of the present invention. In this figure, and indicate deep and shallow channel regions, respectively, and indicates metal deposited by microfabrication techniques. In (A) a proximal heating design is shown, where the heating elements are adjacent to the channel (see inset). An in-channel design is shown in (B), with the inset illustrating the metal strip located within the channel.

A variety of other aspects of design and/or operation of controlled electrokinetic material transport systems are described in the references cited herein and these aspects can be used with the systems, devices, and/or methods of the present invention in specific embodiments. Further, although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays and detection operations. Assay and detection operations include without limitation, probe interrogation assays, e.g., nucleic acid hybridization assays utilizing individual probes, free or tethered within the channels or chambers of the device and/or probe arrays having large numbers of different, discretely positioned probes, receptor/ ligand assays, immunoassays, and the like.

A variety of controlling instrumentation may be utilized in conjunction with the microfluidic devices described above, for controlling the transport and direction of fluids and/or materials within the devices of the present invention. For example, in many cases, fluid transport and direction may be controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

One or more aspects of systems described herein generally include controller systems for use in conjunction with the microfluidic devices typically include an electrical power supply and circuitry for concurrently delivering appropriate voltages to a plurality of electrodes that are placed in electrical contact with the fluids contained within the microfluidic devices or appropriate voltages applied to conductive paths proximal to fluids contained within the devices. Examples of electrical controllers include those described in, e.g., U.S. patent application Ser. No. 08/888, 064 and International Patent Application No. US97/12930 filed Jul. 2, 1997, the disclosures of which are hereby incorporated herein by reference in their entirety for all purposes. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system.

3. Illustrative System Architecture

Figure 3:
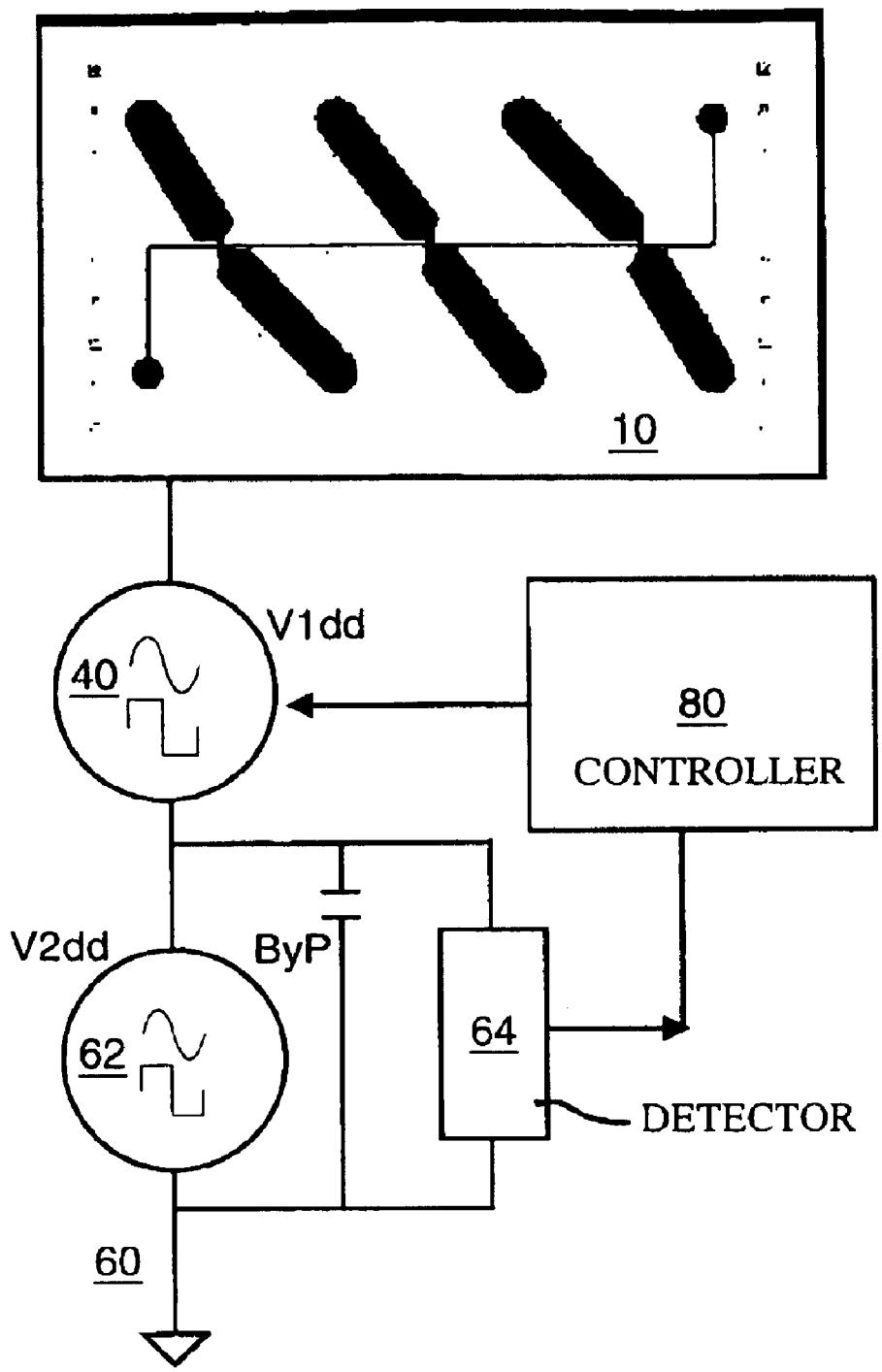
FIG. 3 is a block diagram showing components an illustrative system embodiment for effecting a parameter (e.g., temperature) in a device according to specific embodiments of the present invention.

FIG. 3 is a block diagram showing components an illustrative system embodiment for effecting a parameter (e.g., temperature) in a device according to specific embodiments of the present invention. According to the present invention, two different signals are used, one signal to provide energy for effecting parameters of the sample (e.g., heating, causing an ionizing reaction, moving cells or other material in a sample, etc.) and another signal at a different frequency used as a probe to measure a conductance parameter and to provide feedback to modify the first signal. In specific embodiments, these signals can be used in the same conductive path. Thus, in specific embodiments, the invention provides a mechanism that allows a detection or probe signal to remain separated from an effector signal without requiring physically separate conductive paths.

Specific embodiments generally illustrated by FIG. 2 include (1) a Joule heating system and/or method wherein the effector signal and probe signal are signals through an electrolytic sample medium (2) an in-channel resistive heating system and/or method wherein the effector signal and probe signal are signals through an in-channel electrical conductor; (3) a proximal resistive heating system and/or method wherein the effector signal and probe signal are signals through an electrical conductor proximal to a channel, (4) a cell transport system and/or method wherein the effector signal and probe signal are signals through a cell sample medium. Specific embodiments according to the invention also include (1) a heating system and/or method wherein the effector signal is a DC signal and the probe signal is a distinguishable AC, e.g. of about 10 Hz; and (2) a heating system and/or method wherein the effector signal is a higher frequency AC signal and the probe signal is a distinguishable lower frequency AC signal.

In an example embodiment, a system according to specific embodiments of the present invention can be understood as included four chief components: (1) a LabChip™ 10 or similar device that holds a fluidic or other material that is affected and probed by electrical signals including at least one conductive path for a probe signal and an effector signal; (2) a power source 40 for supplying one or more effector electrical signals that alter parameters at device 10; (4) a probe 60 including a probe signal generator 62 for generating a probe electric signal different than the effector signals and a probe detector 64 for detecting a probe electric signal; and (5) a controller 80 to close a control loop between probe 60 and the controllable power source 40.

Sample Device 10

In particular embodiments, device 10 can be understood as any microscale and/or microfluidic and/or analogous device. As will be understood from the references and discussions herein, such a device includes at least one appropriate conductive path, which in specific embodiments can be either through a sample, in-channel with a sample, or proximal to a sample channel. Methods and systems of according to specific embodiments of the present invention can be used with any sample container, including larger scale samples.

Effector Power Source

Effector power source 40 can comprise any appropriate circuit or device for controllably applying appropriate power levels to have an effect on a sample. It is well-known in the art that all electronic circuits require some source of electric power. Such source can include battery power, locally generated power, or power from a public utility or private utility power grid. In the art of electronic systems, typically a variety of different circuits will be used to generate a desired power signal from an easily available electrical power source (such as from a battery, or 60 Hz, 3-phase 110 volt AC power, or 220 volt power). Many electronic systems include a power supply that for example, inputs 110 volt and/or 220 volt AC power and that converts that power to various different DC voltages for driving the components of an electronic circuit and these can be used according to specific embodiments of the present invention.

In the present invention, in specific embodiments, effector power source 40 refers to any device that is capable of using an available electrical power source and is capable of controllably outputting an effector signal to device 10. For embodiments using DC current, such a power source can be any known electrical circuit configuration for providing a voltage and/or current source that is controllable. In a simple embodiment, control can include simply switching off a power source. In other embodiments, signal power source 40 is a power source that can provide a voltage signal with at least one variable parameter, such as, for example a voltage source with a voltage amplitude that can be varied from about 80 volts down to about 0 volts for resistive heating systems or a voltage source that can be varied from about 3800 volts to about 0 volts for through the sample effects, e.g. Joule heating.

For embodiments using an AC effector signal, effector power source 40 includes some type of frequency generator, also generally with a variable voltage amplitude and possibly with variable current and/or frequency output values.

Probe

Probe 60 comprises a signal source 62 of a particular frequency $f$ and a detector 64 for measuring conductance at the device using the signal source. Many different circuit configurations are known in the art for performing this function. As one example, a number of different off-the-shelf "lock-in amplifier" type circuit devices are available that can be programmed to output a frequency and to measure an impedance detected at that frequency. Depending on the configuration, the detection part of probe 60 can include a by-pass filter as known in the art for diverting power at non-detected frequencies away from the detector.

In specific embodiments, probe 60 can also comprise a spectrum analyzer type device that is able to measure conductance/impedance parameters at a number of different frequencies or a range of frequencies.

Controller

Controller 80 receives output data and/or signal from probe 60 and provides the control function in a feed-back loop to change the effector signal to maintain the desired conductance. A variety of controller feed-backs can be used according to specific embodiments of the present invention, with the complexity determined by specific applications and the desired flexibility of a system. According to specific embodiments of the present invention, controller 80 comprises analog circuits for connecting an output signal from probe 60 to a control input signal of power source 40. In alternative embodiments, controller 80 comprises a programmable and/or digital controller for providing such a feedback and possibly for setting other parameters.

As will be further understood from the following discussion, electrical connections to lab chip 10 of FIG. 3 can be made in various ways. In one embodiment, the applied signals are applied and the detection signal is received over a single connection to device 10 as illustrated in FIG. 3. In alternative embodiments, power source 10 and/or probe signal source 62 and/or probe signal source 64 can be connected at different parts of the conductive path, as further described below.

4. Example Detailed System Architecture for Dual-Signal Control

Figure 4A:
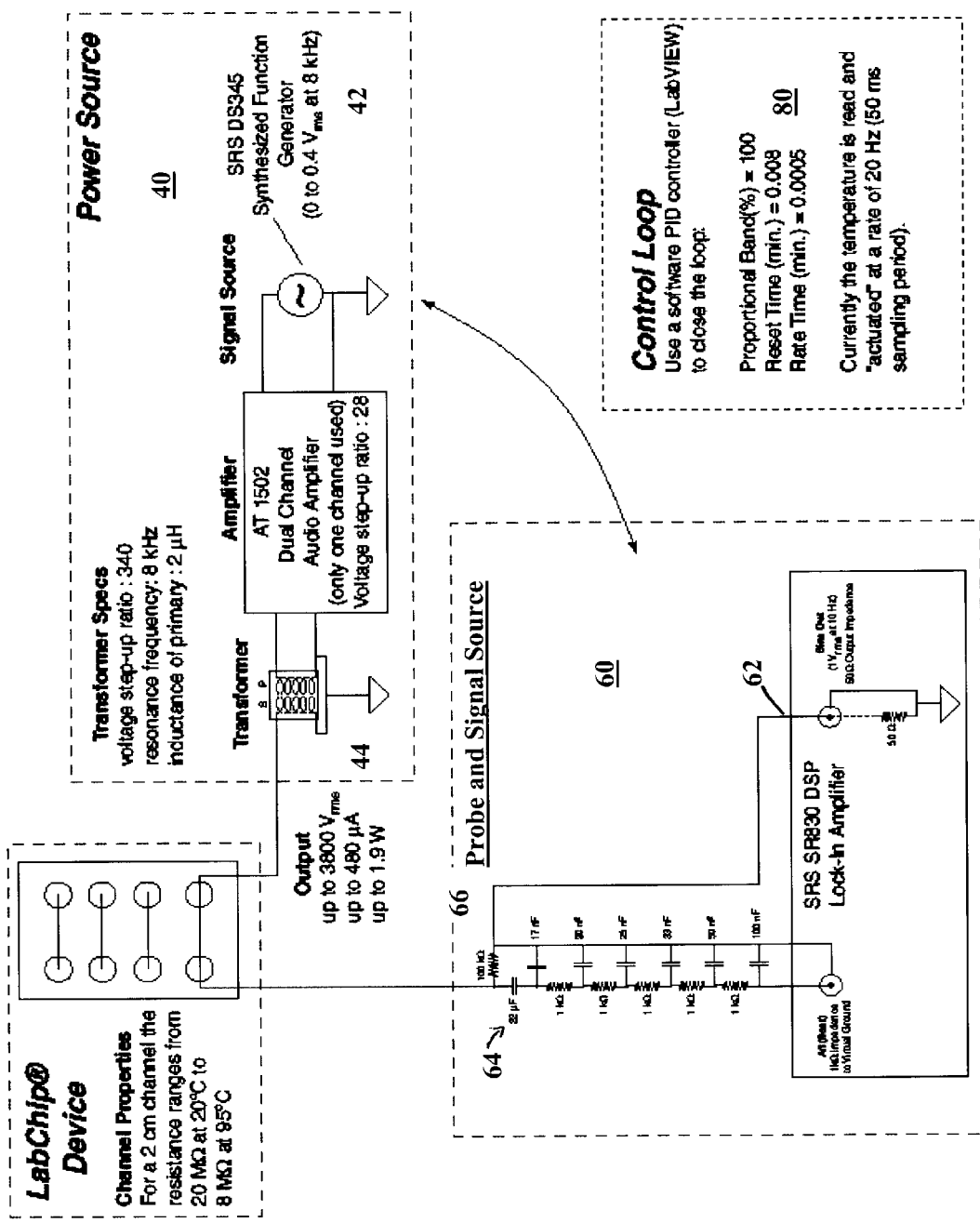
FIG. 4A is a block diagram showing components of a more detailed example system embodiment for controlling Joule heating in a microscale device according to specific embodiments of the present invention.

FIG. 4A is a block diagram showing components of a more detailed example system embodiment for controlling Joule heating in a microscale device according to specific embodiments of the present invention. This figure illustrates an implementation using available off-the-shelf components for system components, operated and modified as herein described.

In the embodiment shown in FIG. 4A, the sample device is represented by a LabChip™ 10 that holds a fluid or other material which is manipulated and probed by electrical signals. Effector power source 40 in this embodiment is an SRS DS345 Synthesized Function Generator. Such a generator is an off-the-shelf device well known in the art and includes a power supply and inputs for controlling the frequency and amplitude of an output signal. In the embodiment shown, an AT 1502 audio amplifier is used to step up the SRS DS345 voltage signal, for example by a factor of 28.

A transformer 44 is further used to increase the voltage sufficiently to achieve a 3800 $V_{rms}$ output desirable for Joule heating embodiments. In resistive heating embodiments, such a transformer generally would not be needed as the maximum voltage output of power source 40 is about 80–100 volts. Operating specifications shown in the figure are given as examples of specific embodiments of the present invention and are not intended to be limiting.

In a specific example embodiment, probe 60 further comprises an SRS SR830 DSP lock-in amplifier 62. This circuit is well known in the art and can be set to provide a desired probe output frequency $f$ (e.g., 10 Hz) at a given voltage. As known in the art, this circuit provides a separate output indicating the output current, which indicates the conductance seen at the output frequency.

The detection circuit, according to specific embodiments of the present invention, further comprises a multi-stage low-pass filter 64. In this example, this filter comprises capacitances 64 and impedances 66. An A/I (amplifier input) 68 (float) 1 k Ohm impedance to Virtual Ground is provided to detect the probe signal that passes through the channel. While these elements are shown as passive capacitors and resistors, it will be understood that the elements are functional designation, so in some embodiments they may be replaced by circuit elements like transistors that perform the same function.

In this example embodiment, controller 80 further comprises a software PID controller (such as LabVIEW) to close the loop. This controller receives a data signal from conductance probe 60 and from that signal determines the desired control signal to output to power source 40.

Figure 4B:
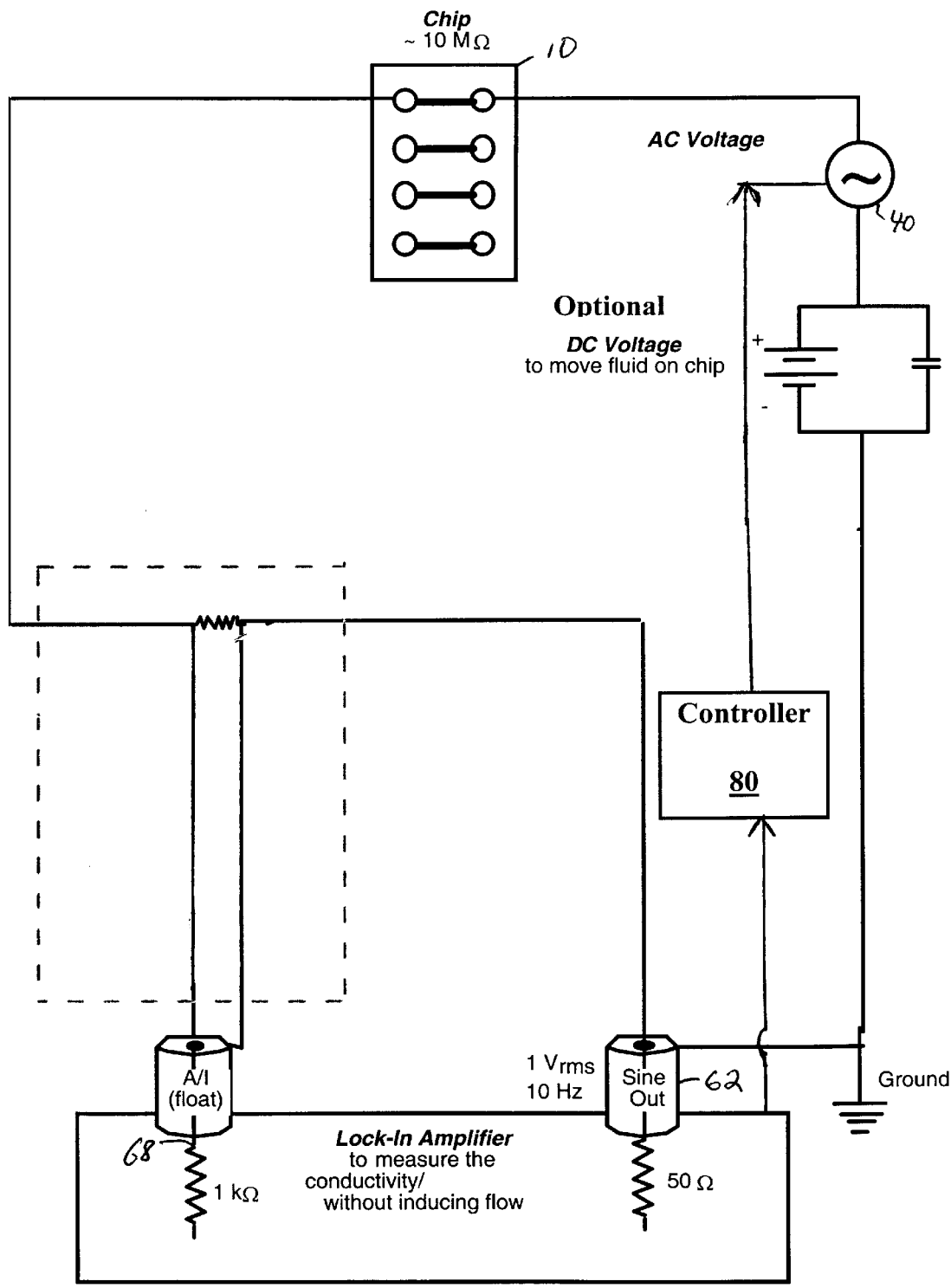
FIG. 4B is a block diagram showing components of an example system embodiment for controlling proximal channel heating in a microscale device according to specific embodiments of the present invention.

FIG. 4B is a block diagram showing components of an example system embodiment for controlling proximal channel heating in a microscale device according to specific embodiments of the present invention. In this figure, because a lower power signal may be used for heating (including a DC signal) the circuit may be simplified in that some of the filtering capacitances and transformer elements are not needed.

5. Example Channel Construction with Single-Loop or Multi-Loop Control

Figure 5A:
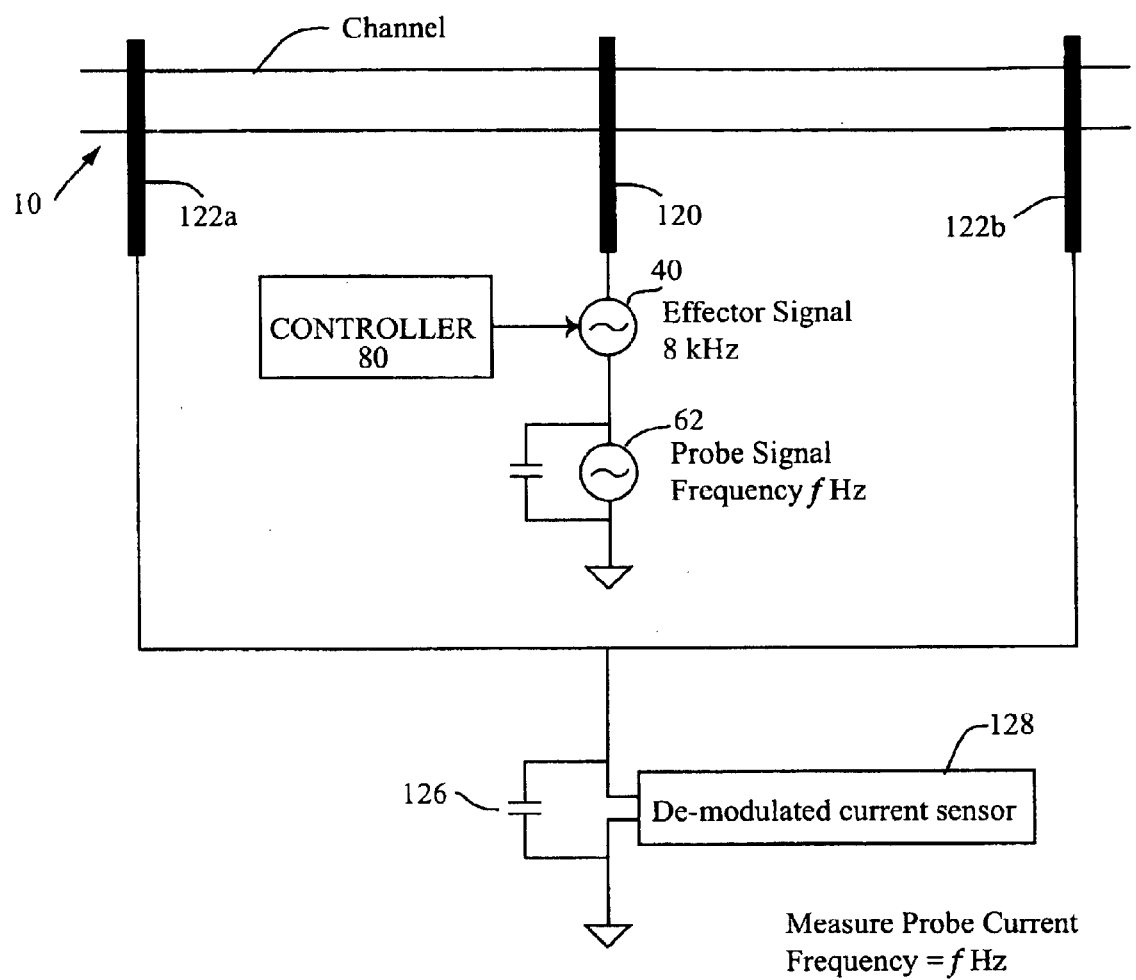
FIG. 5A is a block diagram illustrating a configuration for providing heating in a channel with a central signal electrode and two ground electrodes according to specific embodiments of the present invention.

FIG. 5A is a block diagram illustrating a configuration for providing heating in a channel with a central signal electrode and two ground electrodes according to specific embodiments of the present invention. As can be seen in this example, both a heating signal (e.g., about 8 kHz) and a probe signal (in this example of 10 Hz) can be applied to an electrode 120 in contact with a channel. Both of these signals go to ground through a first electrode 122a and an optional second electrode 122b. However, the heating signal is passed directly to ground through a filter (in this example, a capacitor 126). The probe frequency enters a demodulated current sensor 128, where current is measured. As will be understood from the teachings herein, a control loop (not shown) can then be used from the current sensor to control application of the heating signal. A by-pass capacitor is shown in this example around the probe signal generator for isolating the probe signal generator from the heating signal. In various embodiments of the invention, a system and/or method according to the invention can involve a low frequency signal in a range of about 5–15 Hz and a high frequency signal of about 5–15 kHz.

Figure 5B:
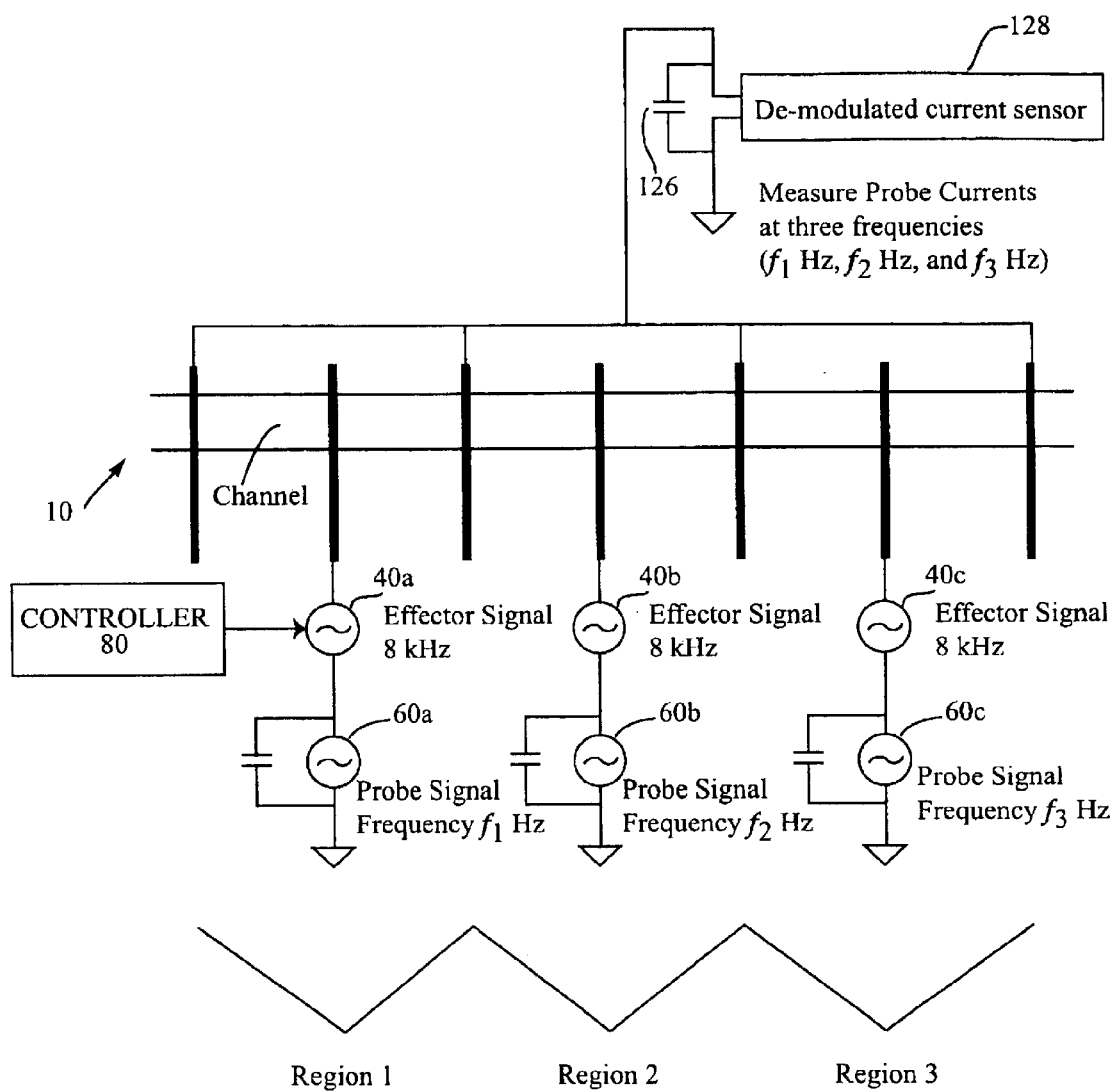
FIG. 5B is a block diagram illustrating a configuration for providing heating in a channel with a three separate control loops according to specific embodiments of the present invention.
Figure 5C:
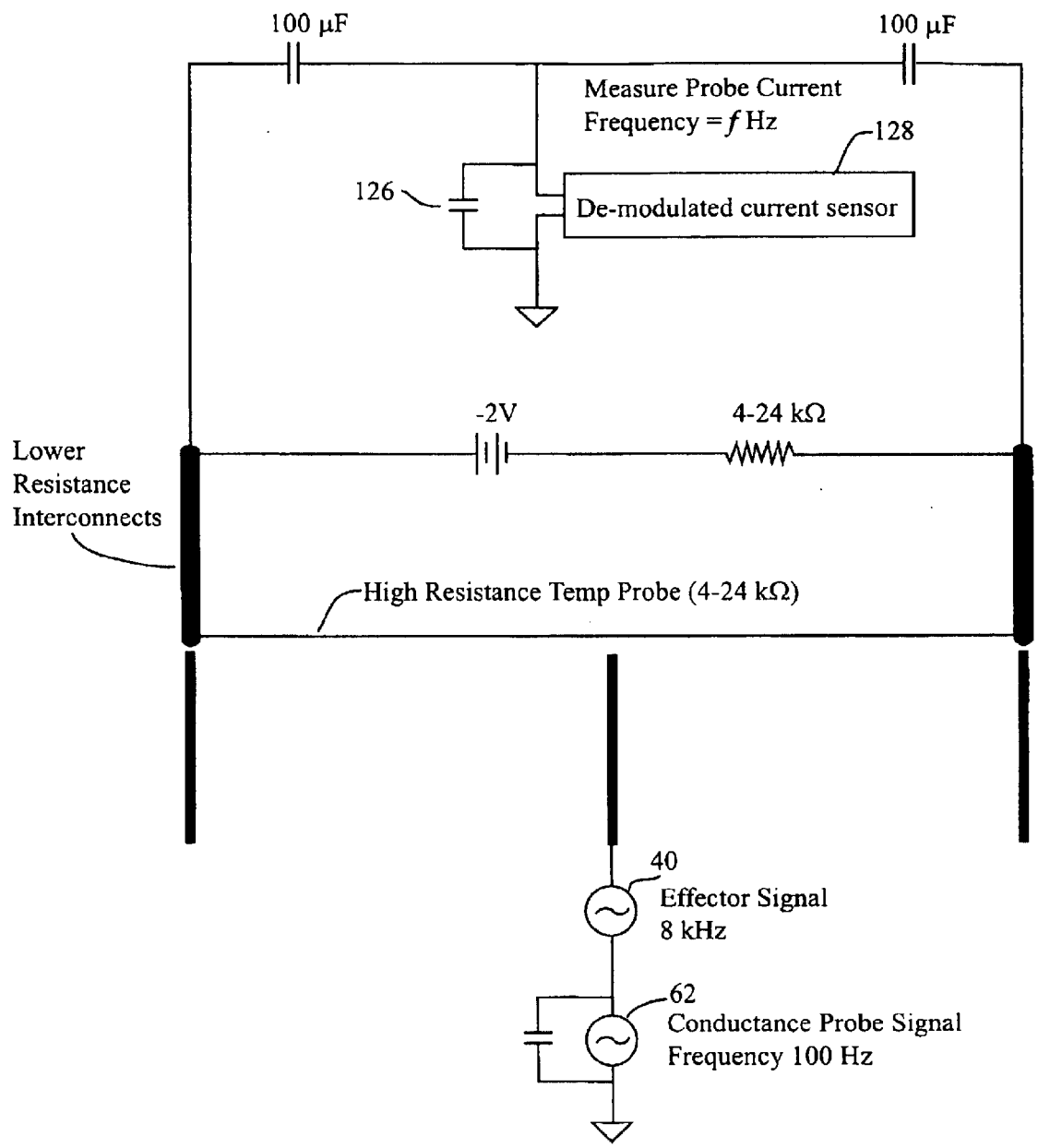
FIG. 5C is a block diagram illustrating a configuration for providing heating in a channel with some modifications from the system shown in 4A according to specific embodiments of the present invention.

FIG. 5B is a block diagram illustrating a configuration for providing heating in a channel with a three separate control loops according to specific embodiments of the present invention. In this embodiment, effectively three control loops are used to control the three heating signal sources, to establish three heating regions in the channel.

6. Using AC Signals for In-Channel Resistive Heating

According to specific embodiments of the present invention, a first AC signal is used for in-channel resistive heating with a second AC signal used for probing heat achieved. Using such a system allows optimum selection of the AC frequency to keep the signal in the conductive path without substantially entering the sample fluid.

7. Example Controller

Figure 6:
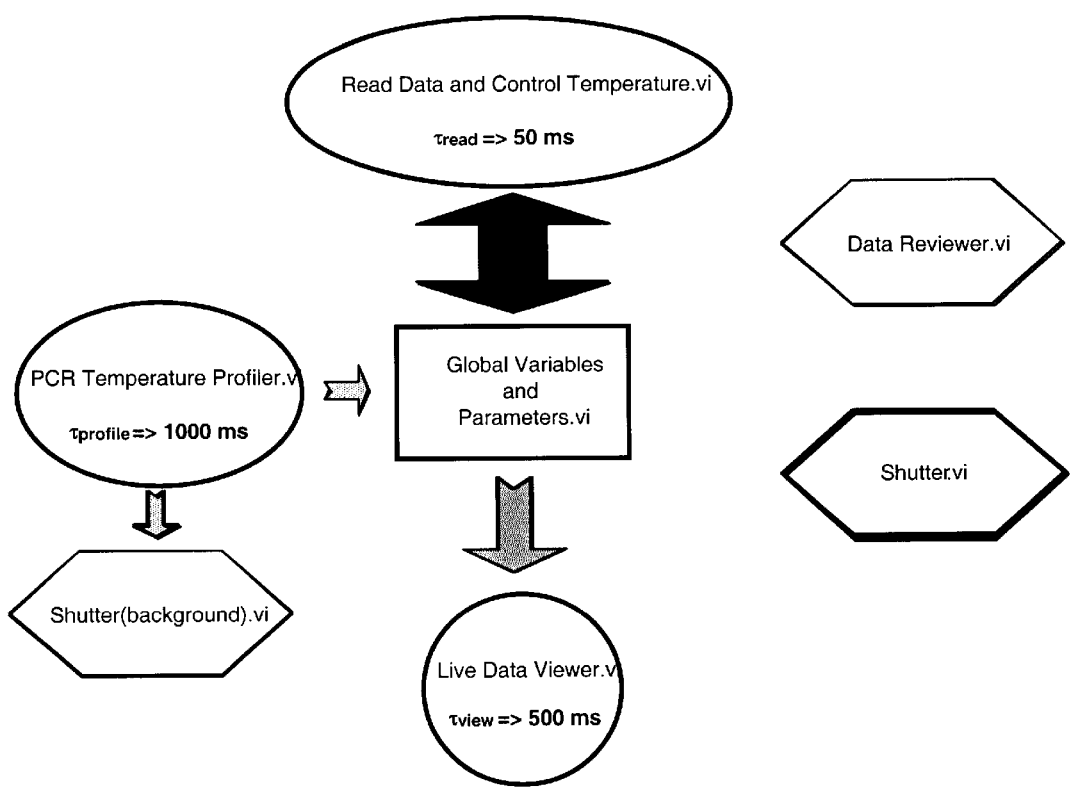
FIG. 6 is a block diagram illustrating software modules that can be used as a controller to operate an AC heater according to specific embodiments of the present invention.

According to various specific embodiments of the present invention, a controller uses the detected probe signal parameter to control the effector signal(s). As an example, software written in LabVIEW can be used to control the temperature (and, optionally further to acquire fluorescence data from the microscope). The temperature was controlled with a PID subroutine package. FIG. 6 is a flow diagram illustrating how the LabVIEW subVIs (LabVIEW programs are referred to as VIs for virtual instruments, and subVIs are subroutines.) are organized and communicate to operate the AC heater. The arrows represent communication links to the various other subVIs; their size and shading are indicators of how fast they talk to each other. According to specific embodiments of the present invention, the functions of each subVI can be generally understood as follows:

Global Variables and Parameters.vi

This is a place where all the variables that describe the system (experimental parameters) and where all the data that is changing on a continual basis that needs to be shared between subVIs (living variables) are stored.

The Experimental Parameters Are:

DAQ Device
ADC Channels
DAC Output Channel
DAC Shutter Channel
Lock-In Sensitivity
Function Generator Amplitude ($V_{rms}$)
Reference Temperature (° C.)
Reference Conductivity (° C.)
Filename
Comments The Living Variables Are:

Temperature Setpoint (° C.)
Lock-In Voltage Setpoint
Lock-In Voltage Output
%Output
Binary Data (data read from ADC inputs with $0-2^{12}$ (4096) full scale)
Cycle#
Status Cluster (Temperature, Time, and Shutter State)

Read Data & Control Temperature.vi

This module reads in the data/voltages from the PMT(s) (Photo Multiplier Tubes for detecting fluorescence) and the Lock-In amplifier and updates the data in the living variables section of Global Variables and Parameters.vi. In addition, this program controls the temperature by changing the output from the function generator. The % Output is the percentage of the amplitude displayed on the front panel of the function generator that is going into the amplifier/transformer circuit.

Live Data Viewer.vi

This program can be used to continually display data such as: temperature, temperature setpoint, % output, and the fluorescence signal read on channels A and B. It obtains the data from the Global Variables and Parameters.vi at the user specified rate. When the program stops, it prompts the user to save the data to a file.

PCR Temperature Profiler.vi

This program changes the temperature setpoint (and voltage setpoint) in Global variables and Parameters.vi to generate the temperature profile inputted by the user. The user selects a state, which consists of a temperature setpoint, hold time, and a shutter state (open or closed). States can be chosen for a hard melt, final extension, and a series of states which can be programmed to cycle through any number of times. When the cycling is completed, the program changes the temperature setpoint to 20° C. to leave the system in a safe, low voltage state.

Shutter.vi

Toggles the shutter state by changing the voltage on the DAC out pin. There are two versions of this subVI, one that the PCR Temperature Profiler calls, "Shutter (background) .vi," and one that the operator uses to manually open and close the shutter, "Shutter.vi." The user only needs to open "Shutter.vi."

Data Reviewer.vi

Opens data from the designated file and plots it up in the same format as in the Live Data Viewer.vi. This is not essential for operation, but is a convenient feature when you want to revisit old data.

According to specific embodiments of the present invention, Data Reviewer.vi and Shutter.vi are independent of the other subVIs. Thus, only the programs that are enclosed by heavy lines need to be open when using the heater for PCR on a chip.

8. Other Example Microfluidic System Characteristics

Many variations in the overall design of microscale systems are possible. It will be understood from the teachings herein that heating and controlling according to specific embodiments of the present invention can be incorporated into such variations. Details of variations in microscale systems are discussed in the cited references. Some characteristics of various microscale system are discussed further below.

Example General Detection Methods

In the microfluidic systems described herein, a variety of detection methods and systems may be employed, depending upon the specific operation that is being performed by the system. Often, a microfluidic system will employ multiple different detection systems for monitoring the output of the system. Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer. As noted above, and as described in greater detail below, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an AD/DA converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

Temperature Control in Microfluidic Systems

As noted previously, the present invention in particular embodiments involves microfluidic systems that selectively provide energy to heat materials, e.g., fluids, including samples, analytes, buffers and reagents, in a desired location (s), e.g., within selected channels and/or chambers, of the microfluidic device in an efficient manner. In particular, the present invention uses power source(s) that passes electrical current through fluid that is disposed within the channels and/or chambers of microfluidic systems, for heating that material in a controlled manner. The present invention, therefore, takes the art recognized problem of resistive electrical heating of fluids in electrically controlled systems, and utilizes it to the advantage of the experimenter, e.g., to perform heating and control operations, within microfluidic systems.

To provide more precise control of heating, including allowing for more rapid heating, in further embodiments, the invention involves the use of a second probe electrical signal to detect temperature characteristics of a sample. This second signal, in specific embodiments, is an electrical signal having a different frequency than the signal used for heating. Thus, in specific embodiments, the invention provides a mechanism that allows a detection or probe signal to remain separated from an effector signal without requiring physical separation.

The methods and systems of the present invention provide a multitude of advantages over typical temperature control methods for fluidic systems. For example, such systems provide an ease of control and automation that come with precise electrical control of the temperature. Further such systems provide advantages of speed in changing temperatures of fluids and materials within channels. Additionally, these systems are readily integrated into state of the art electrokinetic microfluidic systems. Finally, such methods and systems permit the precise regional control of temperature control and/or heating within separate microfluidic elements of a given device, e.g., within one or several separate channels in a given device, without heating other regions where such heating is less desired. In particular, in accordance with the presently described methods and systems, heat is only generated within the fluidic elements where such heating is desired. Further, because such microfluidic elements are extremely small in comparison to the mass of the substrate in which they are fabricated, such heat remains substantially localized, e.g., it dissipates into and from the substrate before it affects other fluidic elements. In other words, the relatively massive substrate functions as a heat sink for the separate fluidic elements contained therein. Thus, in accordance with the present invention, one can selectively heat materials in one or more channels of an integrated microfluidic channel system, e.g., having multiple intersecting channels, or multiple channels that are closely packed together on a single substrate or body structure, while not substantially altering the temperature of material in other channels on the substrate or intersecting with the heated channel.

In some of the embodiments, a portion of the power goes into kinetic energy of moving the fluid through the channel and a selected portion of the power to heat the fluid in the channel or a selected channel region(s). This channel region may be narrower or smaller in cross-section than other channel regions in the channel structure. The smaller cross-section provides higher resistance in the fluid, which increases the temperature of the fluid as electric current passes therethrough. Alternatively, the electric current can be increased along the length of the channel by increased voltage, which also increases the amount of power dissipated into the fluid to correspondingly increase fluid temperature.

Figure 7:
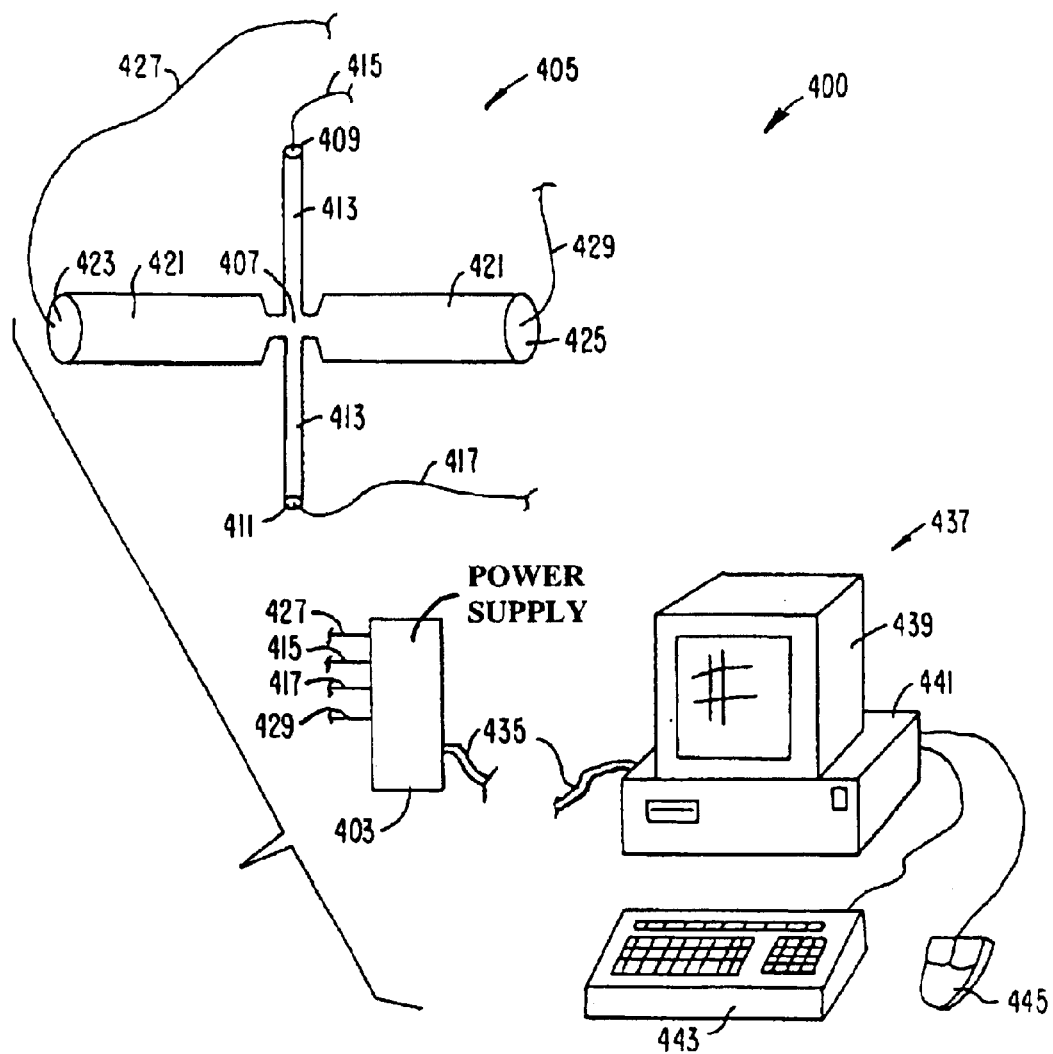
FIG. 7 is a simplified diagram of a microfluidic system with a heating source according to the present invention.

FIG. 7 is a simplified diagram of one example of a microfluidic system 400 with a heating source according to the present invention. The diagram is merely an illustration and should not limit the scope of the claims herein. One of ordinary skill in the art would recognize other variations, alternatives, and modifications. The diagram illustrates a channel network or configuration 405 for moving and heating a volume of material, e.g., fluid, in channel or capillary region 407, which is located at the intersection of channels 413 and 421. Channel 413 can have a similar length and width such as those described herein, but can also be others. Channel 413 connects to regions 409 and 411. Regions 409 and 411 supply power to channel 413 for moving the fluid between regions 409 and 411. Material is moved between these regions by electrokinetic effects, e.g., electroosmotic and/or electrophoretic forces, such as those previously described herein, but is not limited to these effects. Power supply 403 provides power through lines 415 and 417 to regions 409 and 411, respectively. In particular, power supply 403 provides a voltage differential or electric field between regions 409 and 411 by application of a voltage differential to electrodes in regions 409 and 411, which voltage differential drives the electrokinetic movement of the material. As shown, the voltage differential applies along the length of channel 413.

Preferably, power supply 403 also provides power to regions 423 and 425 for the purpose of heating the fluid and material in region 407 in the channel configuration. In particular, power supply 403 provides a voltage differential between regions 423 and 425, resulting in an electric current between regions 423 and 425. The electric current is used to distribute energy to the fluid and material in region 407 for at least heating purposes. Channel 421 includes a novel geometric configuration, which is designed to effectively heat the fluid in region 407 in an efficient manner. As shown, channel 421 includes outer portions 421, each having a larger width or cross-sectional (e.g., diameter) dimension than inner portion or region 407, which has a corresponding larger fluid or electrical resistance than outer portions 421. The precise dimensions of the wider and narrower portions can be optimized depending upon the amount of current applied through the system, the amount of desired heating, the thermal capacity of the substrates and the like, which can be easily optimized experimentally. In any event, such dimensions typically fall within the dimensions described for microscale channels, herein, e.g., at least one cross-sectional dimension between 0.1 and 500 µm.

To selectively control the temperature of fluid or material at region 407 of the channel, power supply 403 applies voltage and/or current in one of many ways. For instance, power supply 403 applies direct current (i.e., DC), which passes through channel 421 and into channel region 407 which is smaller in cross-section to heat fluid and material in region 407. This direct current can be selectively adjusted in magnitude to complement any voltage or electric field that may be applied between regions 409 and 411 to move materials in and out of region 407. In order to heat the material within region 407, without adversely affecting the movement of that material, alternating current (i.e., AC) can be selectively applied by the power supply 403 through channel 421 and into channel region 407 to heat fluid in region 407. This alternating current used to heat the fluid can be selectively adjusted to complement voltage or electric field that may be applied between regions 409 and 411 to move fluid in and out of region 407. AC current, voltage, and/or frequency can be adjusted, for example, to heat the fluid without substantially moving the fluid. Alternatively, power supply 403 applies a pulse or impulse of current and/or voltage, which passes through channel 421 and into channel region 407 to heat fluid in region 407 at a given instance in time. This pulse can be selectively adjusted to complement any voltage or electric field that may be applied between regions 409 and 411 to move materials, e.g., fluids or other materials, in and out of region 407. Pulse width, shape, and/or intensity can be adjusted, for example, to heat the fluid substantially without moving the fluids or materials, or to heat the material while moving the fluid or materials. Still further, the power supply may apply any combination of DC, AC, and pulse, depending upon the application.

A controller or computer 437 such as a personal computer, commonly termed PC, monitors the temperature of the fluid in region 407 of the channel. The controller or computer receives current and voltage information from, for example, the power supply and identifies or detects temperature of fluid in region 407 in the channel. Depending upon the desired temperature of fluid in region 407, controller or computer adjusts voltage and/or current to meet the desired fluid temperature. The controller or computer also can be set to be "current controlled" or "voltage controlled" or "power controlled" depending upon the application. Controller or computer 437 includes a monitor 439, which is often a cathode ray tube ("CRT") display, a flat panel display (e.g., active matrix liquid crystal display, liquid crystal display), and others. Computer circuitry is often placed in a box 441, which includes numerous integrated circuit chips, such as a microprocessor, memory, interface circuits, and others. The box 441 also includes a hard disk drive, a floppy disk drive, a high capacity drive (e.g., ZipDrive.TM. sold by Iomega Corporation), and other elements. Also shown are keyboard 443 and mouse 445, which provide for a human interface to computer box 441. A variety of techniques by way of a computer program can be used to detect and monitor temperature, as well as other process parameters. Some of these techniques are described in more detail below.

In some embodiments, computer 437 is coupled to a network such as a local or wide area network. The local network can be configured as, for example, Ethernet or Token Ring. The local area network can also be an "Intranet." Any one or a combination of these local area networks can be connected to a wide area network such as the "Internet" among others. The network can also be wireless, depending upon the application. The network allows for users to be off-site or allows multiple users to monitor or control or view processes of the present microfluidic system.

The embodiment shown in FIG. 7, for example, provides a higher fluid or material temperature in the channel at region 407 than at peripheral regions 421. Fluid in channel region 421 is maintained at temperature T0. Fluid in channel region 407 is maintained at temperature Ts The fluid temperature at region 407 is higher than the fluid temperature at region 421 as a result of the higher current density (and higher resistance) at region 407 from the cross-section of the channel at region 407 being smaller relative to the cross-section of the channel in region 421. Depending upon the shape of the channel, the temperature profile from one end of the channel to the other end of the channel can vary selectively. As can be appreciated, temperature control along the length of the channel can be varied by varying the cross-sectional dimension of that channel, while allowing the current to remain unchanged.

Example Geometric Variations

Figure 8:
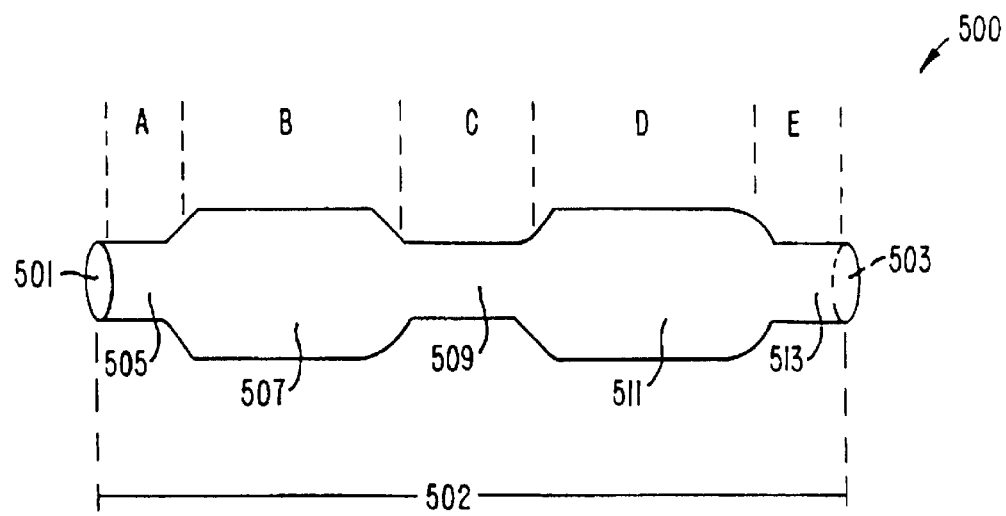
FIG. 8 is a simplified diagram of a microfluidic system with a heating source according to an alternative embodiment of the present invention.

FIG. 8 is a simplified diagram of a microfluidic system with a heating source according to an alternative embodiment of the present invention. FIG. 7 illustrates, as one example, a simplified diagram of a microfluidic system 500 with a heating source according to an alternative embodiment of the present invention. This diagram is merely an illustration and should not limit the scope of the claims herein. One of ordinary skill in the art would recognize other variations, alternatives, and modifications. The microfluidic system 500 includes a channel 502 having a variety of temperature zones, e.g., A, B, C, D, E, and fluid therein.

A first power supply, such as the one described above, provides electric current between regions 501 and 503 for the purpose of heating fluid in region 505, 509 and 513 of the channel configuration. The power supply also provides a voltage differential between regions 501 and 503 that drives the transport of material through channel 502. The electric current is used, at least in part, to distribute energy to fluid in region 509 for at least heating purposes. The power supply (or another power supply) can also drive or move fluid between regions 501 and 503. A second signal source provides a probe signal between 501 and 503 as described herein.

Channel 502 includes one type of geometric configuration, which is designed to heat the fluid in region 505, 509 and 513 in an efficient manner. As shown, channel 502 includes outer portions 507, 511 that each has a larger width or cross-section dimension than inner portion or region 509. Additionally, regions 505 and 513 that attach, respectively, to regions 501 and 503, each has a smaller width or cross-section dimension than outer portions 507 and 511. The narrower dimensions result in an increased current density within these regions when a current is passed through channel 502, resulting in a heating of the fluid located within these regions. Accordingly, fluid also increases in temperature in regions 505 and 513. Material can also be transported from region 501 to 503 while being heated in region 509, allowing heating of only a portion of the material. Further, additional regions of narrower dimension are optionally provided along the length of channel 502, to provide thermal cycling, "on the fly," as material is transported along channel 502. Other geometric configurations are discussed in the cited references and these can also be used with a heating system and/or method according to specific embodiments of the present invention.

In a specific embodiment, fluid is heated in certain regions and cools in other regions. In particular, fluid in regions 507 and 511 is cooler than fluid in regions 505, 509, and 513. Additionally, channel 502 can be coupled to other channels, which move fluid from one region of channel 502 to another region of channel 502. Still further, the power supplied between regions 501 and 503 can be varied depending upon the application. For instance, the power source supplies energy in the form of electric current and/or voltage across regions 501 and 503. The electric current and/or voltage can be DC, AC, pulsed, a combination thereof, and others. Of course, the type of power used depends upon the application.

A variety of methods can be used to globally raise or lower fluid temperature in the microfluidic system, using energy sources or sinks to affect this temperature change. These methods are described in cited references.

Numerous techniques can be used to control power to the microchannels for the purpose of moving the fluid. These techniques can also be used to selectively monitor and adjust temperature in the microchannels or annular regions, as well. As noted above, one example of one of these techniques is the use of a processor or controller and/or computer software such as the one described above. Alternatively, exclusively hardware or preferably a combination of hardware and software can perform these techniques. Details with regard to specific computer programs that can perform selected techniques according to the present inventions are described below.

In a specific embodiment, the present invention provides a technique used to detect and control temperature of a fluid being heated in a microchannel by way of current and/or voltage and/or impedance measurements. Depending upon the application, other techniques may also be used. These techniques, of course, depend upon the application. The present technique may be briefly described by way of the following sequence of steps:

(1) Flow fluid in channel of microfluidic system;

(2) Stop flow of fluid in microchannel (optional);

(3) Apply first electric signal through conducting path to heat fluid;

(3) Apply probe electric signal through conducting path to probe temperature of fluid;

(4) Measure parameters of probe electric signal;

(5) Calculate temperature from probe electric signal;

(6) Compare actual temperature based upon a desired temperature set-point;

(8) Adjust first electric signal applied based upon a difference between the actual temperature and the desired temperature set-point.

The above sequence of steps can be performed using, for example, a computer program. The computer program provides an easy-to-use method to perform the above steps in a microfluidic system. The computer program can be executed in the form of computer software, firmware, hardware, or combinations thereof. The program executes the above functions using an interface that is coupled to the microfluidic system. The interface receives signals from the microfluidic system and provides signals to, for example, the power source, which supplies electric current to fluid for heating purposes.

In a modification to the preceding embodiment, the global or overall temperature of the microfluidic system can be raised or lowered during any one of the above process steps. Overall fluid temperature is preferably globally raised or lowered using the technique described above, but can be others. Accordingly, fluid can be moved from one region to another in the microfluidic system. Fluid movement can be combined with selective heating of the fluid at a selected portion of a microchannel and/or global fluid heating of the entire microfluidic system. Additionally, the fluid in the microfluidic system can be static and heated globally or selectively in a specific location of the microfluidic system.

The embodiments directed to controlling temperature of fluid can be further modified or controlled by way of an active feedback process or control, using the probe signal, and depending upon the application. The active feedback process generally receives a signal such as temperature from the microfluidic process, for example. The measured temperature is compared with a set-point temperature. A difference is calculated, taking into account any effects necessary for specific applications, such as non-linear relationships between temperature and impedance or additional factors needed for heat conductance when the electrically conductive channel is not in direct contact with the sample. If the measured temperature is less than the set-point, a result based upon a function of the temperature difference is used to control additional current or voltage to the fluid for heating purposes. In preferred embodiments, the function prevents any substantial "overshoot" or "oscillation" of the actual temperature from the set-point temperature. Additionally, the function ensures that the set-point is achieved in an efficient manner. Examples of functions used to provide feedback control include among others, proportional control, differential control, integral control, or a combination thereof.

Using, for example, proportional control, a feedback process according to the present invention provides an active feedback to the process based upon a multiplier. An output of a proportional controller is a fixed multiple of a measured difference or "error." That is, the proportional controller is simply the multiplier. Terms often used in describing proportional controllers include a proportional band and a controller gain. Controller gain is an amount by which the error is multiplied to obtain an output. The controllers can be calibrated to the proportional band rather than the gain depending upon the application.

In a modification to the preceding embodiment, the global or overall temperature of the microfluidic system can be raised or lowered during any one of the above process steps. Overall fluid temperature is preferably globally raised or lowered using the technique described above, but can be others. Accordingly, fluid can be moved from one region to another in the microfluidic system. Fluid movement can be combined with selective heating of the fluid in at a selected portion of a microchannel and/or global fluid heating of the entire microfluidic system. Additionally, the fluid in the microfluidic system can be static and heated globally or selectively in a specific location of the microfluidic system.

Although descriptions herein are generally in terms of flow diagrams, which can be carried out with computer software, the present inventions can also be carried out in many other ways. For instance, the computer software can be placed in hardware such as a memory device, e.g., field programmable gate arrays ("FPGAs"), electrically erasable programmable read only memories ("EEPROMs"), read only memories ("ROMs"), random access memories ("RAMs"), etc. Another type of memory device would be a compact disk read only memories ("CDROMs"), hard disks, floppy disks, high capacity disks (e.g., ZipDrive.TM. sold by Iomega Corporation), and others. Alternatively, the computer software can be placed in a combination of hardware and software. Some of the functions described can be separated, or even combined, depending upon the application. Of course, one of ordinary skill in the art would recognize other variations, modifications, and alternatives, depending upon the particular application.

Various applications of microfluidic devices according to specific embodiments of the present invention will be readily understood from the examples provided in the cited references. For example, various processes for Amplifying and Detecting Nucleic Acids are described in e.g., U.S. Pat. Nos. 4,683,195; 4,683,202; and 4,965,188; PCR Technology: Principles and Applications for DNA Amplification (ed. Erlich, Freeman Press, New York, N.Y., 1992); PCR Protocols: A Guide to Methods and Applications (eds. Innis et al., Academic Press, San Diego, Calif. (1990); Mattila et al. Nucleic Acids Res. 19:4967 (1991); Eckert & Kunkel PCR Methods and Applications 1:17 (1991); PCR (eds. McPherson et al., IRL Press, Oxford) (each of which is incorporated by reference in its entirety for all purposes). Reagents, apparatus, and instructions for using the same are commercially available. Other amplification systems include the ligase chain reaction, QB RNA replicase and RAN-transcription-based amplification systems.

While the foregoing invention has been described in some detail for purposes of clarity and understanding, it will be clear to one skilled in the art from a reading of this disclosure that various changes in form and detail can be made without departing from the true scope of the invention. For example, all the techniques described above may be used in various combinations. All publications and patent documents cited in this application are incorporated herein by reference in their entirety for all purposes to the same extent as if each individual publication or patent document were so individually denoted.

9. Embodiment in a Programmed Information Appliance

Figure 9:
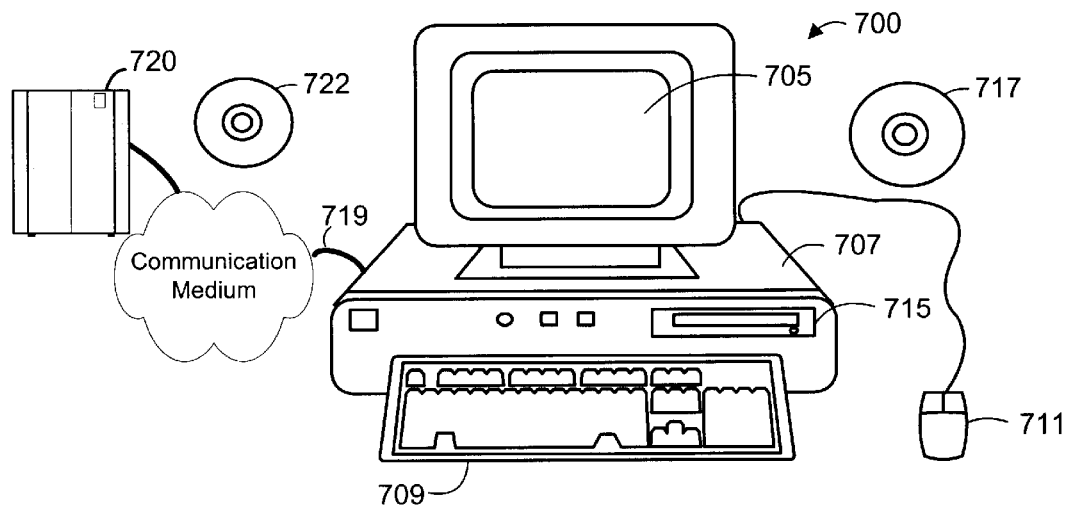
FIG. 9 is a block diagram showing a representative example logic device in which various aspects of the present invention may be embodied.

FIG. 9 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 9 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

10. Other Embodiments

The invention has now been described with reference to specific embodiments. Other embodiments will be apparent to those of skill in the art. In particular, a viewer digital information appliance has generally been illustrated as a personal computer. However, the digital computing device is meant to be any information appliance for interacting with a remote data application, and could include such devices as a digitally enabled television, cell phone, personal digital assistant, etc. Thus, although the present invention has been described in terms of various specific embodiments, it is not intended that the invention be limited to these embodiments. Modification within the spirit of the invention will be apparent to those skilled in the art. It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed:

1. A method of elevating temperature in at least a portion of a fluid-filled channel disposed in a substrate, to a selected elevated temperature, comprising:

applying a first selectable current through a fluid in the at least a portion of the fluid-filled channel, the portion of the fluid-filled channel having an electrical resistance;

applying a second selectable current through the fluid in the at least a portion of the fluid-filled channel, wherein the second selectable current has a different frequency than the first selectable current, detecting at least one characteristic indicative of a temperature of the fluid using the second selectable current; and using the opt characteristic to control at least one of the selectable current or the electrical resistance to elevate the temperature of the fluid in the portion of the channel to the selected elevated temperature.

2. The method of claim 1, further wherein: the first selectable current comprises a higher frequency, higher voltage signal; and the second selectable current comprises a lower frequency, lower voltage signal.

3. The method of claim 1, further wherein: the first selectable current comprises a higher frequency signal of about 10 kHz; and the second selectable current comprises a lower frequency signal of about 10 Hz.

4. The method of claim 1, further wherein: the second selectable current is used to measure the conductivity of the channel.

5. The method of claim 1, further wherein: the first selectable current comprises a frequency signal of greater than about 300 Hz.

6. The method of claim 1, wherein the portion of the channel is at least a first portion and the selected elevated temperature is a first selected elevated temperature, and further comprising maintaining at least a second portion of the channel at a second temperature lower than the first selected elevated temperature.

7. The method of claim 6, further comprising: providing the first portion of the channel with a narrowed cross-sectional area relative to the second portion of the channel; and wherein the controlling step comprises applying a constant current through a fluid in the first and second portions of the channel.

8. The method of claim 6, comprising repeatedly transporting a material between the at least first portion of the channel and the at least second portion of the channel to cycle a temperature of the material between the first selected elevated temperature and the second temperature.

9. The method of claim 8, wherein the material comprises reagents for performing a nucleic acid amplification reaction.

10. The method of claim 9, wherein the nucleic acid amplification reaction is selected from the group consisting of a polymerase chain reaction and a ligase chain reaction.

11. The method of claim 8, wherein the transporting of the material comprises electrokinetically transporting the material through the at least first portion.

12. The method of claim 11, wherein the selectable current is a first selectable current, and wherein the step of electrokinetically transporting the material comprises applying a third selectable current through the channel to electrokinetically transport a material along the first channel.

13. The method of claim 12, wherein the first selectable current comprises an alternating current and the third selectable current comprises a direct current.

14. The method of claim 11, wherein electrokinetically transporting the material through the channel comprises electroosmotically transporting the material through the channel.

15. The method of claim 11, wherein electrokinetically transporting the material through the channel comprises electrophoretically transporting the material trough the channel.

16. The method of claim 1, wherein the fluid-filled channel is disposed in a substrate, and further comprising the step of maintaining a global temperature of the substrate at a selected level above or below ambient temperature.

17. The method of claim 1, wherein the channel is a first channel, and the applying stop comprises: providing at least a second channel intersecting the first channel at the portion of the first channel; and applying the first selectable current through the second channel and the portion of the first channel.

18. The method of claim 1, wherein the controlling step further comprises sensing a temperature in the portion of the channel using the second current, and increasing or decreasing the selectable current based upon the temperature sensed.

19. The method of claim 18, wherein the sensing step comprises determining a relative electrical conductivity parameter through the fluid in the portion of the channel, the relative electrical conductivity parameter being indicative of the temperature of the fluid in at least the portion of the channel.

20. A method of elevating temperature in at least a portion of a sample channel disposed in a substrate, to a selected elevated temperature, comprising:
applying a first selectable electric signal through a conducting path associated with the at least a portion of the sample channel, the conducting path having an electrical impedance;
applying a second selectable electric signal trough the conducting path, wherein the second selectable current has a different frequency than the first selectable current;
detecting at least one characteristic indicative of a temperature of the fluid using the second selectable signal; and
using the one characteristic to control elevating the temperature of the conducting path so that the selected elevated temperature of the channel is reached.

21. The method of claim 20, further wherein: the first selectable signal comprises a higher frequency, higher voltage signal; and the second selectable signal comprises a lower frequency, lower voltage signal.

22. The method of claim 20, further wherein: the first selectable signal comprises a higher frequency signal of about 10 kHz; and the second selectable signal comprises a lower frequency signal of about 10 Hz.

23. The method of claim 20, further wherein: the first selectable signal comprises a DC signal; and the second selectable signal comprises an AC frequency signal.

24. The method of claim 20, further wherein: the second selectable signal is used to measure the conductivity of the channel.

25. The method of claim 20, further wherein: the first selectable signal comprises a frequency signal of greater than about 300 Hz.

26. The method of claim 20, further wherein: the conducting path comprises an electrolytic fluid or gel sample in said channel.

27. The method of claim 20, further wherein: the conducting path comprises a single-path conducting material placed in the channel of the substrate such that at least a portion of the conducting material is in physical contact with a sample placed in the channel.

28. The method of claim 20, further wherein: the conducting path comprises a single-path conducting material placed proximal to the channel of the substrate such that none of the conducting material comes in physical contact with a sample placed in the channel but such that heat in the conducting material is transferred by heat conduction to the sample.

29. The method of claim 20, wherein the controlling step further comprises sensing a temperature in the portion of the channel using the second signal, and increasing or decreasing the selectable first signal based upon the temperature sensed.

30. The method of claim 29, wherein the sensing step comprises determining an electrical conductivity parameter through the conducting path, the relative electrical conductivity parameter being indicative of the temperature of the conducting path and of the portion of the channel.

31. The method of claim 20, wherein the portion of the channel is at least a first portion and the selected elevated temperature is a first selected elevated temperature, and further comprising maintaining at least a second portion of the channel at a second temperature lower than the first selected elevated temperature.

32. The method of claim 31, comprising repeatedly transporting a material between the at least first portion of the channel and the at least second portion of the channel to cycle a temperature of the material between the first selected elevated temperature and the second temperature.

33. The method of claim 32, wherein the material comprises reagents for performing a nucleic acid amplification reaction.

34. The method of claim 33, wherein the nucleic acid amplification reaction is selected from the group consisting of a polymerase chain reaction and a ligase chain reaction.

35. The method of claim 32, wherein the transporting of the material comprises electrokinetically transporting the material through the at least first portion.

36. The method of claim 35, wherein the selectable current is a first selectable current, and wherein the step of electrokinetically transporting the material comprises applying a third selectable signal through the channel to electrokinetically transport a material along the first channel.

37. The method of claim 36, wherein the third selectable signal comprises a direct current.

38. The method of claim 35, wherein electrokinetically transporting the material through the channel comprises electroosmotically transporting the material through the channel.

39. The method of claim 35, wherein electrokinetically transporting the material through the channel comprises electrophoretically transporting the material through the channel.

40. The method of claim 20, wherein the fluid-filled channel is disposed in a substrate, and further comprising the step of maintaining a global temperature of the substrate at a selected level above or below ambient temperature.

41. A method of heating fluid in a microfluidic system, said method comprising steps of;
providing a channel having a first end, a second end, and a region defined therebetween, said channel being disposed in a substrate;
providing fluid in said region of said channel;
applying a first electric current signal through said fluid to heat said fluid at said region;
applying a second electric current signal through said fluid to measure an electrical parameter of said fluid at said region; said electrical parameter correlated with a temperature of said fluid; wherein the second selectable current has a different frequency than the first selectable current, and wherein said first electric current selectively heats said fluid in said region of said channel while preventing substantial heating of said fluid outside said region.

42. The method of claim 41, wherein said channel is an annular region.

43. The method of claim 41, wherein said current is applied using a voltage bias applied directly to said fluid.

44. The method of claim 43, wherein said voltage bias is applied directly to said fluid using a pair of electrodes.

45. The method of claim 41, wherein said region has a smaller cross-section relative to a cross-section of said channel at said first end.

46. The method of claim 41, wherein said region has a smaller cross-section relative to a cross-section of said channel at said second end.

47. The method of claim 41, wherein said fluid contains materials selected from the group consisting of samples, analytes, buffers and reagents.

48. The method of claim 41, wherein said channel comprises a cross-section ranging from about 0.1 micro meters to about 500 micro meters.

49. The method of claim 41, wherein said region is disposed in said substrate adjacent to a second fluid-filled channel disposed in said substrate, but wherein said region is not in direct fluid communication with said second channel.

50. The method of claim 41, further comprising a step of moving said fluid in said channel, said step of moving comprising the steps of applying a voltage bias to said fluid to move said fluid between said first end and said second end.

51. The method of claim 41, wherein said voltage bias is provided by DC.

52. The method of claim 41, wherein said applying step occurs successively to heat and cool said fluid in said region; wherein said applying step selectively heats and cools said fluid in said region of said channel while preventing substantial heating of said fluid outside said region.

53. The method of claim 52, wherein said fluid comprises a nucleic acid material.

54. The method of claim 52, wherein said steps occur in a nucleic acid amplification process.

55. The method of claim 54, wherein the nucleic acid amplification process is selected from the group consisting of PCR and LCR.

56. A method of controlling temperature of fluid in a channel defined in a substrate of a microfluidic system, said method comprising steps of:
applying a first electrical energy source to begin heating said fluid in said channel;
applying a second electrical energy source to probe a detection parameter indicative of a temperature of said fluid in said channel, wherein the second electrical energy source produces a current with a different frequency than the current produced by the first electrical energy source; and
adjusting a first parameter applied from said first electrical energy source to said fluid to provide a relatively constant detection parameter in said fluid, wherein said first parameter is current, voltage, power or a combination thereof, and the detection parameter is resistance and conductivity; and wherein said fluid is heated without substantially increasing a temperature of said substrate.

57. The method of claim 56, wherein said first parameter is voltage.

58. The method of claim 56, wherein said first parameter is electric current.

59. The method of claim 56, wherein said detection parameter is conductivity.

60. The method of claim 56, wherein said applying step occurs successively to heat and cool said fluid in said channel.

61. The method of claim 56, wherein said fluid is heated in a portion of said channel.

62. A system for elevating temperature in at least a portion of a fluid-filled channel disposed in a substrate, to a selected elevated temperature, comprising:
a controllable effector power source able to apply a first controllable signal through a fluid in the at least a portion of the fluid-filled channel;
a probe signal source able to apply a second voltage signal through a fluid in the at least a portion of the fluid-filled channel, wherein the second voltage signal has a different frequency than the first controllable signal;
a probe signal detector able to detect at least one characteristic indicative of a fluid temperature using said probe signal;
and a controller able to use said at least one characteristic to provide a control signal varying said controllable effector power source.

63. The system of claim 62, further wherein: the first controllable signal comprises a higher frequency, higher voltage signal; and the probe signal comprises a lower frequency, lower voltage signal.

64. The system of claim 62, further wherein: the first controllable signal comprises a higher frequency signal of about 10 kHz; and the probe signal comprises a lower frequency signal of about 10 Hz.

65. The system of claim 62, further wherein: the probe signal is used to measure conductance of the channel.

66. The system of claim 62, further wherein: the first controllable signal comprises a frequency signal of greater than about 300 Hz.

* * * * *